United States Patent [19]

Kyncl et al.

[11] 3,947,590
[45] Mar. 30, 1976

[54] COMPOSITIONS AND METHODS OF INCREASING RENAL BLOOD FLOW WITH GAMMA-GLUTAMYL AMIDE OF DOPAMINE

[75] Inventors: Jaroslav Kyncl, Lake Bluff; Kathleen Riley, Gurnee; Yvonne Connolly Martin, Waukegan; Carroll Wayne Ours, Zion, all of Ill.

[73] Assignee: Abbott Laboratories, North Chicago, Ill.

[22] Filed: Jan. 27, 1975

[21] Appl. No.: 544,101

Related U.S. Application Data

[62] Division of Ser. No. 408,902, Oct. 23, 1973, Pat. No. 3,903,147.

[52] U.S. Cl. ............... 424/319; 424/316; 424/233; 424/253; 424/274; 424/280
[51] Int. Cl.[2] ........ A61K 31/20; A61K 31/185; A61K 31/615; A61K 31/52
[58] Field of Search .......... 424/316, 319, 233, 253, 424/274, 280

[56] References Cited
UNITED STATES PATENTS 3,676,492   7/1972   Biel .................................. 260/519
3,790,618   2/1974   Koenig ............................. 260/519
3,859,331   1/1975   Kaiser et al. ...................... 424/319

Primary Examiner—Donald B. Moyer
Attorney, Agent, or Firm—Paul D. Burgauer; Robert L. Niblack

[57] ABSTRACT

Covers a γ-glutamyl amide of dopamine selected from the group consisting of

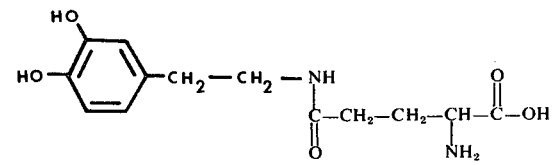

and a pharmaceutically acceptable acid addition salt thereof. Also covers the use of said γ-glutamyl amide to increase renal blood flow by administering said amide to warm-blooded mammals.

4 Claims, No Drawings

COMPOSITIONS AND METHODS OF INCREASING RENAL BLOOD FLOW WITH GAMMA-GLUTAMYL AMIDE OF DOPAMINE

HISTORY OF THIS APPLICATION

This application is a divisional of Ser. No. 408,902, filed by us on Oct. 23, 1973 now U.S. Pat. No. 3,903,147.

BACKGROUND OF THE INVENTION

Dopamine has been reported to be useful in treating congestive heart failure and shock. In addition, certain amino acids of dopamine have been found useful as renal vasodilators and antihypertensive agents. (For example, see U.S. Pat. No. 3,676,492.) However, compounds disclosed in the just-mentioned patent and others which are used as renal vasodilators have the drawback that they also produce undesirable systemic hemodynamic changes.

It would be a distinct advance in the art if a compound could be discovered which has utility as a renal vasodilator but which does not also produce systemic hemodynamic changes such as increase in arterial blood pressure, heart rate, left ventricular systolic pressure, etc.

SUMMARY OF THE INVENTION

We have now discovered compounds which are useful as renal vasodilators, and yet do not produce unwanted hemodynamic changes. In brief, these compounds are γ-glutamyl amides of dopamine selected from the group consisting of

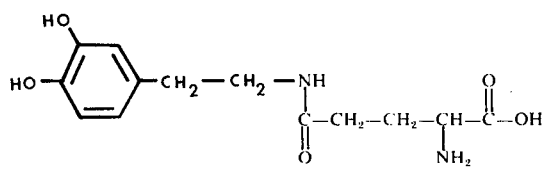

and a pharmaceutically acceptable acid addition salt thereof. We have also discovered a method of increasing renal blood flow of warm-blooded animals by administering to said mammals at least an effective amount of the above renal vasodilator compound. Lastly, we have discovered that useful pharmaceutical compositions may be made using the dopamine amide as the active portion along with a pharmaceutically acceptable carrier.

DETAILED DESCRIPTION OF THE INVENTION

The compounds of the invention may be prepared by a wide variety of methods. The following examples illustrate typical procedures:

EXAMPLE I

Preparation of [$N^5$-β-(3,4-Dihydroxyphenyl)-Ethyl]-Glutamine Hydrochloride

Reaction:

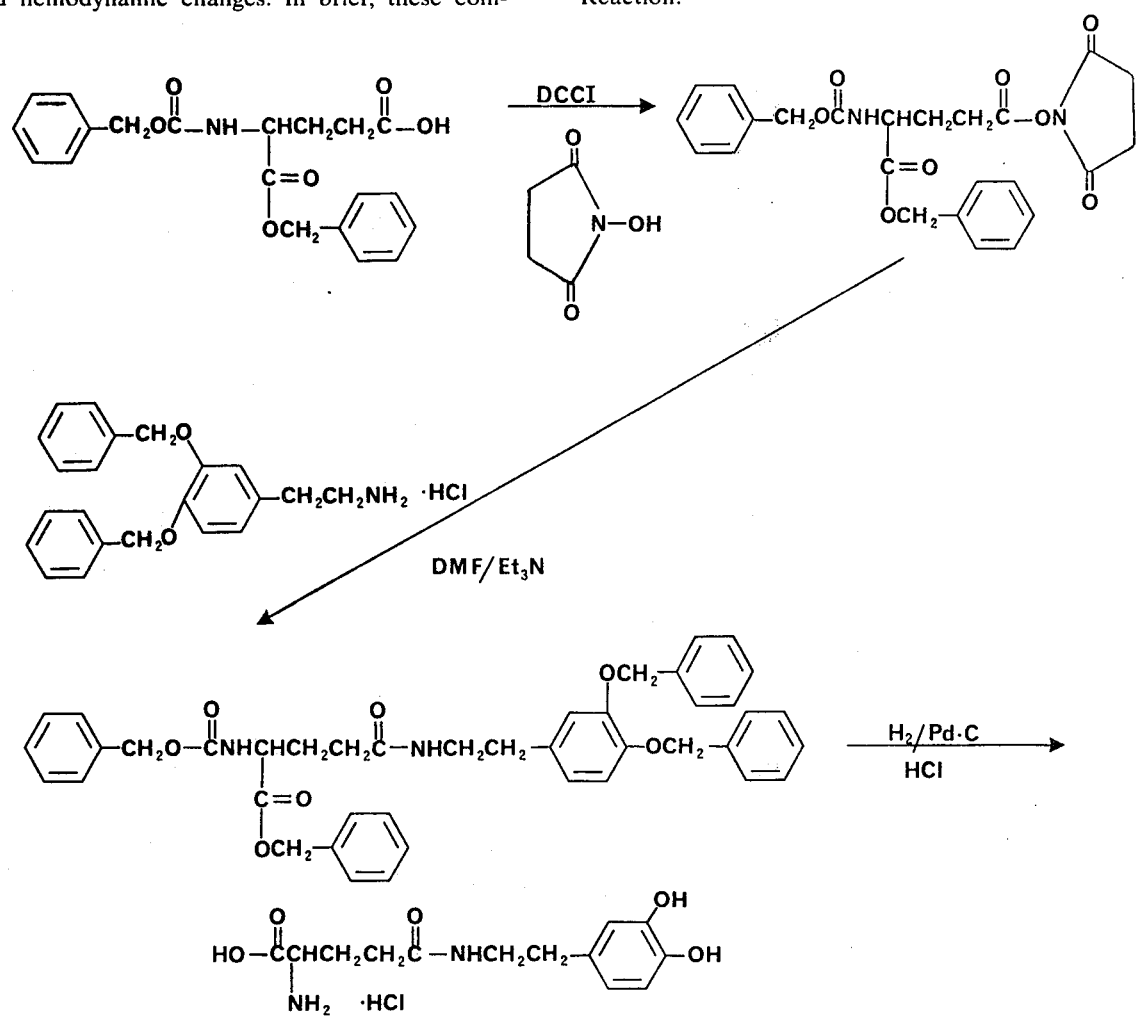

Preparation of N-CBZ-O$^5$-Succinimido-L-Glutamic Acid O-Benzyl Ester

To a solution of N-CBZ-L-glutamic acid-α-benzyl ester (0.057 mole, 21.8 g.) and N-hydroxysuccinimide (0.057 mole, 6.6 g.) in 100 ml. of dioxane was added with stirring at room temperature (0.057 mole, 12.0 g.) of dicyclohexylcarbodiimide. After 24 hours stirring at room temperature the mixture was filtered to remove dicyclohexylurea. The filtrate was concentrated in vacuo to give an oil. This oil was taken up in ethanol: ether (1:2) and cooled to give 22.4 g. (84%) of a crystalline solid, m.p. 104° – 6°.

Preparation of N-CBZ-[N$^5$-β(3,4-Benzyloxyphenyl) Ethyl]-Glutamine O-Benzyl Ester A solution of the active ester (0.048 mole, 22.4 g.) and dibenzyldopamine .HCl (0.048 mole, 17.8 g.) in 100 ml. of DMF was treated with triethylamine (0.1 mole, 14 ml.) and stirred at room temperature for 4 hours. The solution was then diluted with water to give an oil which solidified on standing. The white solid was collected and washed well with water. The moist solid was dissolved in boiling absolute ethanol, filtered and allowed to crystallize. The solid was collected and washed with ethanol to give, after drying at 60° overnight, 29.4 g. of the protected amide, m.p. 126° – 8°.

| Microanalysis for C$_{42}$H$_{42}$N$_2$O$_7$ Molecular weight 686.8 | |
|---|---|
| Calc. % | Found % |
| C 73.45 | 73.52 |
| H 6.16 | 6.27 |
| N 4.08 | 4.13 |

Preparation of [N$^5$-β-(3,4-Dihydroxyphenyl) Ethyl]-Glutamine Hydrochloride A suspension of the protected amide (0.0365 mole, 25 g.) from step 2 was reduced in a Parr apparatus in ethanol containing 5.0 g. 5% Pd.C and 1 eq. of concentrated HCl. After uptake was complete, the catalyst was filtered and washed with ethanol. The filtrate was concentrated in vacuo to give, upon repeated azeotroping with methanol, a glass. This glass was dried under high vacuum at 60° for 24 hours to give 11.3 g. (97%) of [N$^5$-β01J(3,4-dihydroxyphenyl)ethyl]-glutamine.HCl.

| Microanalysis for C$_{13}$H$_{19}$ClN$_2$O$_5$ Molecular weight 318.76 | |
|---|---|
| Calc. % for 1% H$_2$O | Found % |
| C 48.50 | 48.46 |
| H 6.07 | 6.18 |
| N 8.70 | 8.46 |

EXAMPLE II

Preparation of N$^5$-[β-(3-(3,4-Dihydroxyphenyl) Ethyl]-Glutamine

A Parr bottle is charged with 1.6 g. 5% Pd.C catalyst, 150 ml. ethanol and 15.5 g. (0.03 mole) of N-CBZ-[β-(3,4-dibenzyloxyphenyl)ethyl] glutamine O-benzyl ester. This is reduced until a theoretical uptake of H$_2$ is complete. The mixture is diluted with an equal volume of water, filtered and concentrated in vacuo to give a white solid. Crystallizing from methanol (decolorizing with aid of Norite) gives 7.0 g. (80%) of white solid, m.p. 198° – 200° dec.

Microanalysis for C$_{13}$H$_{18}$N$_2$O$_5$.½ H$_2$O = 291.31 g./mole

| Calc. % | Found % |
|---|---|
| C 53.60 | 53.58 |
| H 6.57 | 6.98 |
| N 9.62 | 9.08 |

The compounds of this invention are renal vasodilators and have been found to significantly increase renal blood flow in test animals. The compounds are useful as specific renal vasodilators which may be useful as antihypertensive agents, diuretics, agents used to treat shock and congestive heart failure and compounds used to treat edema, and to detoxify poisons such as barbituates.

Anesthetized dogs were tested to measure the increase in renal arterial blood flow after being administered with a compound of the invention. With regard to the anesthetized dogs, the following test procedure was employed:

Dogs of either sex, weighing between 9 and 15 kg. were anesthetized with barbital sodium (250 mg./kg. intravenously) following sedation with morphine sulfate (3 mg./kg. subcutaneously), 30 minutes earlier. A polyethylene catheter was placed in the abdominal aorta via the femoral artery to monitor the aortic blood pressure. Another polyethylene cannula was advanced into the left ventricular cavity via the left carotid artery to record left ventricular peak systolic pressure (LVSP). Heart rate was counted from lead II electrocardiogram. A precalibrated electromagnetic flow probe (Carolina Medical Electronics) and an occluding cuff were positioned around the right renal artery through a retroperitoneal approach. Zero blood flow was obtained by inflating the occluding cuff for a short period (10–30 seconds). Aortic blood pressure, left ventricular pressure, heart rate and renal blood flows were recorded continuously on a Grass Model 7 Polygraph.

In four anesthetized dogs, dopamine and the compound of Example I, [N$^5$-β-(3,4-dihydroxyphenyl)-ethyl]-glutamine hydrochloride were compared after intravenous injections. Whereas the renal vasodilator action of dopamine (150 μg./kg. i.v.) was accompanied by pronounced increase in arterial blood pressure, heart rate, left ventricular systolic pressure and dp/dt. Comparable increases in renal blood flow after treatment with the subject glutamine hydrochloride were obtained without such changes. In fact one could give a maximum single dosage of the glutamine hydrochloride up to 2500 μg./kg. to increase the renal blood flow for a period of 82.5 ± 5.5 minutes without any systemic cardiovascular action. Thus, as can be seen from Table I below, there is a clear disassociation between the renal vasodilator action and systemic hemodynamic effects for the compound of Example I, but not for dopamine.

Table I

Effect of Intravenous Injection of [N⁵-β-(3,4-Dihydroxyphenyl)-Ethyl]-Glutamine Hydrochloride and Dopamine in the Anesthetized Dogs

| Compound | μg./kg., I.V. | Renal Blood Flow % Change | Duration (min) | Mean Aortic Blood Pressure % Change | Left Ventricular Systolic Pressure % Change | Max. dpDT % Change | Heart Rate % Change |
|---|---|---|---|---|---|---|---|
| Dopamine | 15.0 | 31.3 ±10.3 | 7.5 ±.9 | −15.8 ± 4.8 | −14.6 ± 4.1 | 27.8 ± 9.8 | 14.6 ± 3.9 |
|  | 150.0 | 25.5 ±10.9 | 23.8 ±8.2 | 84.4 ±11.2 | 99.1 ±11.6 | 272.8 ±50.6 | 55.5 ±19.5 |
| Example I [N⁵-β-(3,4-Dihydroxy-phenyl)-Ethyl]-Glutamine Hydrochloride | 25.0 | 2.2 ±4.3 | 6.8 ±1.2 | 0 | 0 | 0 | 0 |
|  | 75.0 | 9.8 ±1.2 | 14.5 ±7.6 | 0 | 0 | 0 | 0 |
|  | 250.0 | 24.0 ±3.1 | 17.8 ±3.0 | 0 | 0 | 0 | 0 |
|  | 750.0 | 32.2 ±5.7 | 41.0 ±9.4 | 0 | 0 | 0 | 0 |
|  | 2,500.0 | 29.6 ±5.8 | 82.5 ±5.5 | 0 | 0 | 0 | 0 |

MEAN ± SEM; N = 4
O Means less than ± 15%

We have also studied the time-course effect of the compound of Example I and dopamine, which effect for said compound differs characteristically and significantly from that of dopamine. The largest single i.v. dose of dopamine which did not produce an overall cardiovascular stimulation (15 μg./kg.) increased the renal blood flow for only 5 – 10 minutes. The compound of Example I, on the other hand, in the highest nonpressor i.v. dose (2500 μg./kg.) increased the renal blood flow for an average of 82 minutes.

In summary then, it has been found that [N⁵-β-(3,4-dihydroxyphenyl)-ethyl]-glutamine hydrochloride is a highly unusual selective renal vasodilator. After administering the compound, one notes the following unusual properties: marked increase in renal blood flow, prolonged duration of action, minimal systemic hemodynamic actions even in extremely large doses, and maintenance of activity even after intraduodenal administration.

The compounds of the invention can be administered in dosages of from about 0.01 mg./kg. up to about 2500 mg./kg. dependent upon the route of administration, either single dose or by infusion.

While the compounds can be administered as a free base, it is generally preferred to employ the compounds as their pharmaceutically acceptable acid addition salts. Such salts are easily prepared by methods known to the art. The base is reacted with either the calculated amount of an organic or inorganic acid in an aqueous miscible solvent, such as acetone or ethanol, with isolation of the salt by concentration and cooling, or with an excess of the acid in an aqueous immiscible solvent, such as ethyl ether or chloroform, with the desired salt separating directly. Exemplary of such organic salts are those made with such acids as maleic, fumaric, benzoic, ascorbic, pamoic, succinic, bismethylenesalicyclic, methylsulfonic, ethanesulfonic, acetic, propionic, tartaric, salicylic, citric, gluconic, lactic, malic, mandelic, innamic, citraconic, aspartic, stearic, palmitic, itaconic, glycolic, p-aminobenzoic, glutamic, benzene sulfonic, cyclohexylsulfamic, and theophylline acetic acids as well as with the 8-halotheophyllines, for example, 8-chlorotheophylline and 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. Also included within the purview of this invention are the nontoxic quaternary ammonium salts which include those formed with alkyl halides (e.g., methyl chloride, isobutyl bromide, dodecyl chloride and cetyl iodide), benzyl halides (e.g., benzyl chloride) and dilower alkyl sulfates (e.g., dimethyl sulfate).

The compounds useful in the practice of the present invention are generally formulated into pharmaceutical compositions comprising, as an active ingredient, at least one of the active agents in association with a pharmaceutical carrier or diluent. The compounds useful in the practice of the invention exhibit both oral and parenteral activity and can be formulated in dosage forms for oral or parenteral administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, sweetening and flavoring agents, and the like. In the case of capsules, for example, the active agent may be the sole ingredient.

Liquid dosage forms for oral administration include pharmaceutically acceptable emulsions, solutions, suspensions, syrups, and elixirs containing inert diluents commonly used in the art, such as water. Besides inert diluents, such compositions can also include adjuvants, such as wetting agents, emulsifying and suspending agents, and sweetening, flavoring and perfuming agents.

Preparations according to this invention for parenteral administration include sterile aqueous or nonaqueous solutions, suspensions or emulsions. Examples of nonaqueous solvents or vehicles are propylene glycol, polyethylene glycol, vegetable oils, such as olive oil and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

The dosage of active ingredient in the composition of this invention may be varied; however, it is necessary that the amount of the active ingredient shall be such that a suitable dosage form is obtained. The selected dosage depends upon the desired therapeutic effect, on the route of administration, and on the duration of the treatment.

The following further illustrates pharmaceutical compositions in oral dosage form:

In order to prepare capsules, the following procedure was employed: Specifically, here sufficient pharmaceutical composition was formulated to prepare 1000 capsules. 25.00 g. of [$N^5$-$\beta$-(3,4-dihydroxyphenyl)-ethyl]-glutamine hydrochloride was preblended with 212.5 g. of lactose, U.S.P. and 12.5 g. of talc, U.S.P. The preblend was then passed through a suitable screen and the screened powders were then blended. The powders were then filled into gelatin size No. 3 capsules. The filled weight of 10 capsules was 2.50 g. The filled capsules were then cleaned with sodium chloride.

The following formulation is a typical tablet formula which may be used to incorporate the compound:

Table II

| Ingredient | Amount/Tablet |
| --- | --- |
| Starch U.S.P. Corn | 13 mg. |
| [$N^5$-$\beta$-(3,4-dihydroxyphenyl)-ethyl]-glutamine hydrochloride | 50 mg. |
| Calcium Phosphate Dibasic NF Dihydrate | 132 mg. |
| Water Purified U.S.P. Distilled | q.s. |
| Magnesium Stearate | 1 mg. |
| Talcum (Talc U.S.P.) Powder | 4 mg. |
| | 200 mg. |

Tablets are prepared by using the above formula as follows: First a granulating step is carried out. Here a starch paste is made by adding 8 mg. of cornstarch to water and then heating. The compound is then milled with 5 mg. of additional cornstarch in an equal volume of calcium phosphate dibasic through a 40 mesh screen into a mass mixer. After sufficient mixing the balance of the calcium phosphate dibasic is milled through the 40 mesh screen and thereafter added to the mixer.

The hot cornstarch paste is then also added to the mixer and mixing is carried out until a granular stage is reached. In some instances additional warm water may be added, if necessary. Granulation is carried out through a ⅝inch band. The granulated mixture is dried in a hot air oven at 50° C. overnight to 1.0% L.O.D. (Brabender ½ hr.). After drying the mixture is sifted and then ground to 16 mesh.

Lubricating is carried out by charging half of the granulation into a blender. Talc and magnesium stearate are screened through a 30 mesh screen and charged into the blender. The remainder of the granulation is added and blended 15 minutes.

In order to form tablets compression of the granulated material is carried out by using a 9/32 inch standard convex punch. The resultant tablets have a hardness of 7 - 9 and 10 tablets weigh 2.00 g.

We claim:

1. A method of increasing renal blood flow of warm-blooded mammals which comprises administering to said mammals at least an effective amount of a renal vasodilator compound comprising a γ-glutamyl amide of dopamine selected from the group consisting of

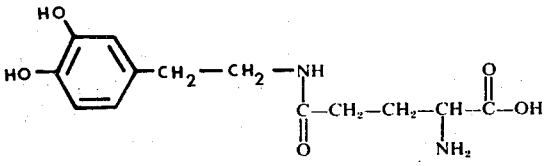

and a pharmaceutically acceptable acid addition salt thereof.

2. The method of claim 1 wherein said salt is a hydrochloride salt.

3. A pharmaceutical composition in unit dosage form effective in increasing renal blood flow which comprises an active portion comprising a γ-glutamyl amide of dopamine selected from the group consisting of

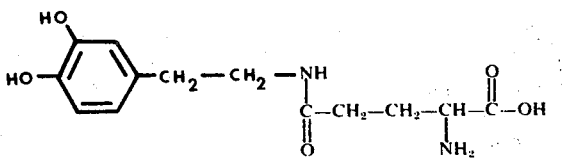

and a pharmaceutically acceptable acid addition salt thereof; and a pharmaceutically acceptable carrier.

4. The composition of claim 3 wherein said amide is a hydrochloride salt.

* * * * *